(12) United States Patent
Yanoff et al.

(10) Patent No.: US 11,389,125 B1
(45) Date of Patent: Jul. 19, 2022

(54) SYSTEM AND METHOD FOR MITIGATING TRACE TRIGGERING OF CHANNELS IN X-RAY DETECTOR

(71) Applicant: GE PRECISION HEALTHCARE LLC, Wauwatosa, WI (US)

(72) Inventors: Brian David Yanoff, Schenectady, NY (US); Biju Jacob, Niskayuna, NY (US)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 0 days.

(21) Appl. No.: 17/168,335

(22) Filed: Feb. 5, 2021

(51) Int. Cl.
- *A61B 6/00* (2006.01)
- *G01T 1/24* (2006.01)
- *G01T 1/172* (2006.01)

(52) U.S. Cl.
CPC ............ *A61B 6/4241* (2013.01); *G01T 1/241* (2013.01); *G01T 1/244* (2013.01); *G01T 1/247* (2013.01); *G01T 1/172* (2013.01)

(58) Field of Classification Search
CPC ....... A61B 6/4241; G01T 1/241; G01T 1/244; G01T 1/247; G01T 1/172
See application file for complete search history.

(56) References Cited

U.S. PATENT DOCUMENTS

| | | | | |
|---|---|---|---|---|
| 4,313,127 A | * | 1/1982 | Su | H01L 27/14875 257/227 |
| 6,815,791 B1 | * | 11/2004 | Dierickx | H01L 31/0352 257/461 |
| 2010/0140491 A1 | * | 6/2010 | Herrmann | H01L 27/14658 250/370.09 |
| 2013/0037899 A1 | * | 2/2013 | Popp | H01L 27/1463 257/429 |
| 2014/0226083 A1 | | 8/2014 | Dunphy et al. | |
| 2018/0090535 A1 | * | 3/2018 | Fujii | H01L 27/14663 |
| 2018/0321394 A1 | * | 11/2018 | Danielsson | G01T 1/241 |
| 2018/0329083 A1 | * | 11/2018 | Danielsson | G01T 1/241 |
| 2019/0383955 A1 | | 12/2019 | Hjärn et al. | |
| 2020/0328321 A1 | * | 10/2020 | Rivetti | H01L 31/117 |

* cited by examiner

*Primary Examiner* — Blake C Riddick
(74) *Attorney, Agent, or Firm* — Fletcher Yoder, P.C.

(57) ABSTRACT

An X-ray detector is provided. The X-ray detector includes multiple detector sub-modules. Each detector sub-module includes a semiconductor layer and multiple detector elements. A first detector element of the multiple detector elements includes a first electrode disposed on a first doped implant and a second detector element of the multiple detector elements includes a second electrode disposed on a second doped implant. The first and second detector elements are disposed on the semiconductor layer adjacent to each other with a gap therebetween. Each detector sub-module also includes wiring traces extending from one or more detector elements of the multiple detector elements to readout circuitry. The wiring traces are routed within the gap between the first and second electrodes. The first doped implant extends underneath a portion of the wiring traces is configured to shield the wiring traces from electrical activity occurring underneath due to absorption of an X-ray.

8 Claims, 9 Drawing Sheets

SYSTEM AND METHOD FOR MITIGATING TRACE TRIGGERING OF CHANNELS IN X-RAY DETECTOR

BACKGROUND

The subject matter disclosed herein relates to X-ray detectors and, more particularly, to mitigating undesired signals originating from the interconnecting wire traces in an X-ray detector.

Non-invasive imaging technologies allow images of the internal structures or features of a subject (patient, manufactured good, baggage, package, or passenger) to be obtained without physical contact.

For example, in X-ray-based imaging technologies, X-ray radiation penetrates a subject of interest, such as a human patient, and a portion of the radiation impacts a detector where the intensity data is collected. In digital X-ray systems, a detector produces signals representative of the amount or intensity of radiation impacting discrete pixel regions of a detector surface. The signals may then be processed to generate an image that may be displayed for review.

In one such X-ray based technique, known as computed tomography (CT), a scanner may project fan-shaped or cone-shaped X-ray beams from an X-ray source at numerous view angle positions about an object being imaged, such as a patient. The X-ray beams are attenuated as they traverse the object and are detected by a set of detector elements which produce signals representing the intensity or number of incident X-rays reaching the detector. The signals are processed to produce data representing the line integrals of the linear attenuation coefficients of the object along the X-ray paths. These signals are typically called "projection data" or just "projections". By using reconstruction techniques, such as filtered backprojection, images may be generated that represent a cross sectional slice or three dimensional volume of a region of interest of the patient or imaged object. In a medical context, pathologies or other structures of interest may then be located or identified from the reconstructed images or rendered volume.

There is a general need for improved X-ray detector designs, and for improved image quality and/or reduced radiation doses.

BRIEF DESCRIPTION

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

In an embodiment, an X-ray detector is provided. The X-ray detector includes multiple detector sub-modules. Each detector sub-module includes a semiconductor layer and multiple detector elements. A first detector element of the multiple detector elements includes a first electrode disposed on a first doped implant and a second detector element of the multiple detector elements includes a second electrode disposed on a second doped implant. The first and second detector elements are disposed on the semiconductor layer adjacent to each other with a gap therebetween. Each detector sub-module also includes wiring traces extending from one or more detector elements of the multiple detector elements to readout circuitry. The wiring traces are routed within the gap between the first and second electrodes. The first doped implant extends underneath a portion of the wiring traces and is configured to shield the wiring traces from electrical activity occurring underneath due to absorption of an X-ray.

In another embodiment, an X-ray detector is provided. The X-ray detector includes multiple detector sub-modules. Each detector sub-module includes a semiconductor layer and multiple detector elements disposed on the semiconductor layer. Each detector sub-module also includes wiring traces extending from the multiple detector elements to readout circuitry. Each detector element is coupled to a respective wiring trace. The wiring traces are routed within a gap between adjacent detector elements of the plurality of detector elements. The X-ray detector also includes processing circuitry configured to perform coincidence detection to determine which detector element of the multiple detector elements is associated with a location of an X-ray hit when the X-ray coincidently hits one of the detectors elements and one or more of the wiring traces coupled to respective detector elements of the multiple detector elements.

In a further embodiment, a method for reducing electrical coupling of wiring traces to an underlying semiconductor layer for an X-ray detector is provided. The method includes subjecting the X-ray detector to a first exposure of X-rays prior to imaging an object utilizing the X-ray detector. Each detector sub-module includes a semiconductor layer and multiple detector elements. A first detector element of the multiple detector includes a first electrode and a second detector element of the multiple detector elements includes a second electrode. The first and second electrodes being disposed on the semiconductor layer adjacent to each other with a gap therebetween. Each detector sub-module also includes wiring traces extending from one or more detector elements of the multiple detector elements to readout circuitry. The wiring traces are routed within the gap between the first and second electrodes. The first exposure of X-rays creates an accumulated charge near a surface of the semiconductor layer underneath the wiring traces. The method also includes utilizing the X-ray detector during a second exposure of X-rays when imaging the object while electrical coupling between the wiring traces and a portion of the semiconductor layer underlying the wiring traces is reduced due to the first exposure of X-rays, wherein the electrical coupling is reduced due to the accumulated charge repelling charges of a same polarity induced by the second exposure of X-rays underneath6 the wiring traces.

BRIEF DESCRIPTION OF THE DRAWINGS

These and other features, aspects, and advantages of the present subject matter will become better understood when the following detailed description is read with reference to the accompanying drawings in which like characters represent like parts throughout the drawings, wherein.

DETAILED DESCRIPTION

Figure 1:
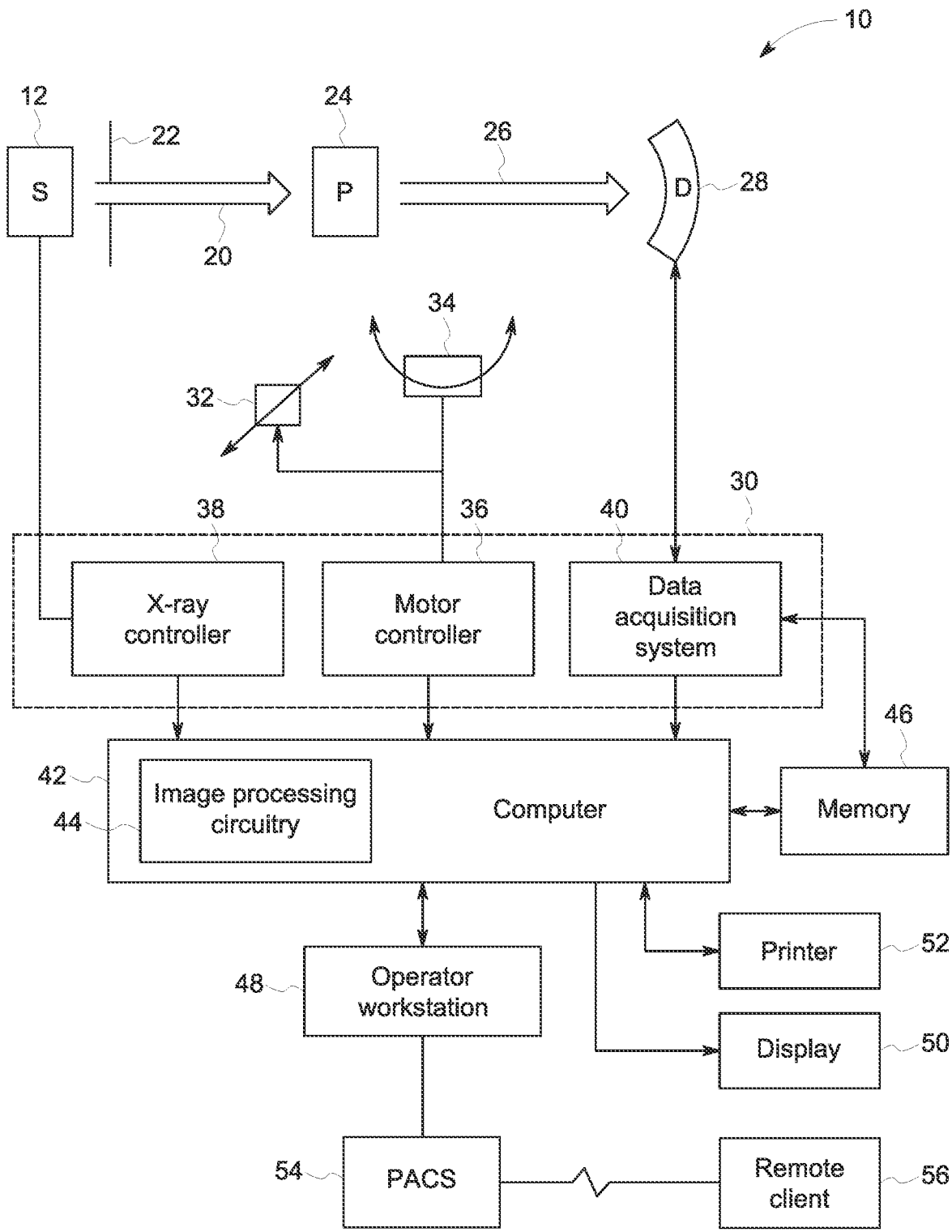
FIG. 1 is a block diagram representation of a CT system, in accordance with aspects of the present disclosure.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

While the following discussion is generally provided in the context of medical imaging, it should be appreciated that the present techniques are not limited to such medical contexts. Indeed, the provision of examples and explanations in such a medical context is only to facilitate explanation by providing instances of real-world implementations and applications. However, the present approaches may also be utilized in other contexts, such as the non-destructive inspection of manufactured parts or goods (i.e., quality control or quality review applications), and/or the non-invasive inspection of packages, boxes, luggage, and so forth (i.e., security or screening applications). In general, the present approaches may be desirable in any imaging or screening context in which a photon-counting detector is utilized.

Energy-resolved, photon-counting detectors can provide spectral information that is not available with conventional energy-integrating detectors. One type of energy-discriminating, photon-counting detection technology employs silicon strips as a direct-conversion sensor material. Use of silicon as the direct-conversion material may provide a higher count rate capability than may be obtained with other direct-conversion materials, such as CZT or CdTe. In certain embodiments, the detector may be arranged edge-on to increase absorption efficiency by enabling an absorption depth to be chosen to any length and the detector can still be fully depleted without going to very high voltages. However, the arrangement of detector elements on detector sub-modules or sensors (in particular those detector elements along an edge of the detector sub-module or sensor) may result in wiring traces being routed along paths distant from the detector element (e.g., pixel). X-rays absorbed in the detector sub-module or sensor beneath the routing may induce signals on the traces (hereafter referred to as trace triggering) resulting in a non-local crosstalk effects (i.e., signals attributed to the wrong detector element).

The present approaches address these effects by mitigating trace triggering of channels (e.g., readout channels) and, thus, mitigating or eliminating crosstalk effects. These techniques improve the performance of silicon-based photon-counting detectors, such as computed tomography detectors or other suitable types of radiographic X-ray detectors.

With the preceding discussion in mind, FIG. 1 illustrates an embodiment of an imaging system 10 for acquiring and processing image data in accordance with aspects of the trace triggering mitigating approaches discussed herein. Although the following embodiments are discussed in terms of the computed tomography (CT) imaging system, the embodiments may also be utilized with other imaging systems (e.g., X-ray, PET, CT/PET, SPECT, nuclear CT, etc.). In the illustrated embodiment, system 10 is a computed tomography (CT) system designed to acquire X-ray projection data, to reconstruct the projection data into a tomographic image, and to process the image data for display and analysis. The CT imaging system 10 includes one or more X-ray sources 12, such as one or more X-ray tubes or solid-state emission structures which allow X-ray generation at one or more locations and/or one or more energy spectra during an imaging session.

In certain implementations, the source 12 may be positioned proximate to a collimator 22 used to define the size and shape of the one or more X-ray beams 20 that pass into a region in which a subject 24 (e.g., a patient) or object of interest is positioned. The subject 24 attenuates at least a portion of the X-rays. Resulting attenuated X-rays 26 impact a detector array 28 formed by a plurality of detector elements (e.g., pixels). As discussed herein, the detector 28 may be a photon-counting detector, including an energy-discriminating photon-counting detector, whose outputs convey information about the number and energy of photons that impact the detector at measured positions and over a time interval corresponding to a scan or imaging session. In certain such embodiments, the energy-discriminating, photon-counting detector may be a direct-conversion type detector (i.e., not employing a scintillator intermediary), such as a detector based on silicon strips. In certain embodiments, the detector array 28 may be formed by a plurality of detector sub-modules or sensors (each having a plurality of detector elements). In certain embodiments, the detector array 28 and the detector sub-modules may be an edge-on detector and edge-on detector sub-modules configured for edge illumination from the X-rays (i.e., the X-rays enter through the edge of the detector sub-modules). In particular, the detector array 28 may be structured similar to the detectors disclosed in U.S. Publication No. 2019/0383955 filed Feb. 19, 2019 and titled "X-ray Detector System Design", which is incorporated herein in its entirety for all purposes.

Each detector element produces an electrical signal that represents the intensity of the incident X-ray photons (e.g., the energy and number of incident photons) at the position of the detector element when the beam strikes the detector 28. Electrical signals are acquired and processed to generate one or more scan datasets.

A system controller 30 commands operation of the imaging system 10 to execute examination and/or calibration protocols and to process the acquired data. With respect to the X-ray source 12, the system controller 30 furnishes power, focal spot location, control signals and so forth, for the X-ray examination sequences. The detector 28 is coupled to the system controller 30, which commands acquisition of the signals generated by the detector 28. In addition, the system controller 30, via a motor controller 36, may control operation of a linear positioning subsystem 32 and/or a rotational subsystem 34 used to move components of the imaging system 10 and/or the subject 24. The system controller 30 may include signal processing circuitry and associated memory circuitry. In such embodiments, the memory circuitry may store programs, routines, and/or encoded algorithms executed by the system controller 30 to operate the imaging system 10, including the X-ray source 12, and to process the data acquired by the detector 28 in accordance with the steps and processes discussed herein. In one embodiment, the system controller 30 may be implemented as all or part of a processor-based system such as a general purpose or application-specific computer system.

The source 12 may be controlled by an X-ray controller 38 contained within the system controller 30. The X-ray controller 38 may be configured to provide power and timing signals to the source 12. In addition, in some embodiments the X-ray controller 38 may be configured to selectively activate the source 12 such that tubes or emitters at different locations within the system 10 may be operated in synchrony with one another or independent of one another.

The system controller 30 may include a data acquisition system (DAS) 40. The DAS 40 receives data collected by readout electronics of the detector 28, such as sampled analog signals from the detector 28. The DAS 40 may then convert the data to digital signals for subsequent processing by a processor-based system, such as a computer 42. In other embodiments, the detector 28 may convert the sampled analog signals to digital signals prior to transmission to the data acquisition system 40. The computer may include processing circuitry 44 (e.g., image processing circuitry). The computer 42 may include or communicate with one or more non-transitory memory devices 46 that can store data processed by the computer 42, data to be processed by the computer 42, or instructions to be executed by a processor (e.g., processing circuitry 44) of the computer 42. For example, the processing circuitry 44 of the computer 42 may execute one or more sets of instructions stored on the memory 46, which may be a memory of the computer 42, a memory of the processor, firmware, or a similar instantiation.

The computer 42 may also be adapted to control features enabled by the system controller 30 (i.e., scanning operations and data acquisition), such as in response to commands and scanning parameters provided by an operator via an operator workstation 48. The system 10 may also include a display 50 coupled to the operator workstation 48 that allows the operator to view relevant system data, imaging parameters, raw imaging data, reconstructed data, and so forth. Additionally, the system 10 may include a printer 52 coupled to the operator workstation 48 and configured to print any desired measurement results. The display 50 and the printer 52 may also be connected to the computer 42 directly or via the operator workstation 48. Further, the operator workstation 48 may include or be coupled to a picture archiving and communications system (PACS) 54. PACS 54 may be coupled to a remote system 56, radiology department information system (RIS), hospital information system (HIS) or to an internal or external network, so that others at different locations can gain access to the image data.

Figure 2:
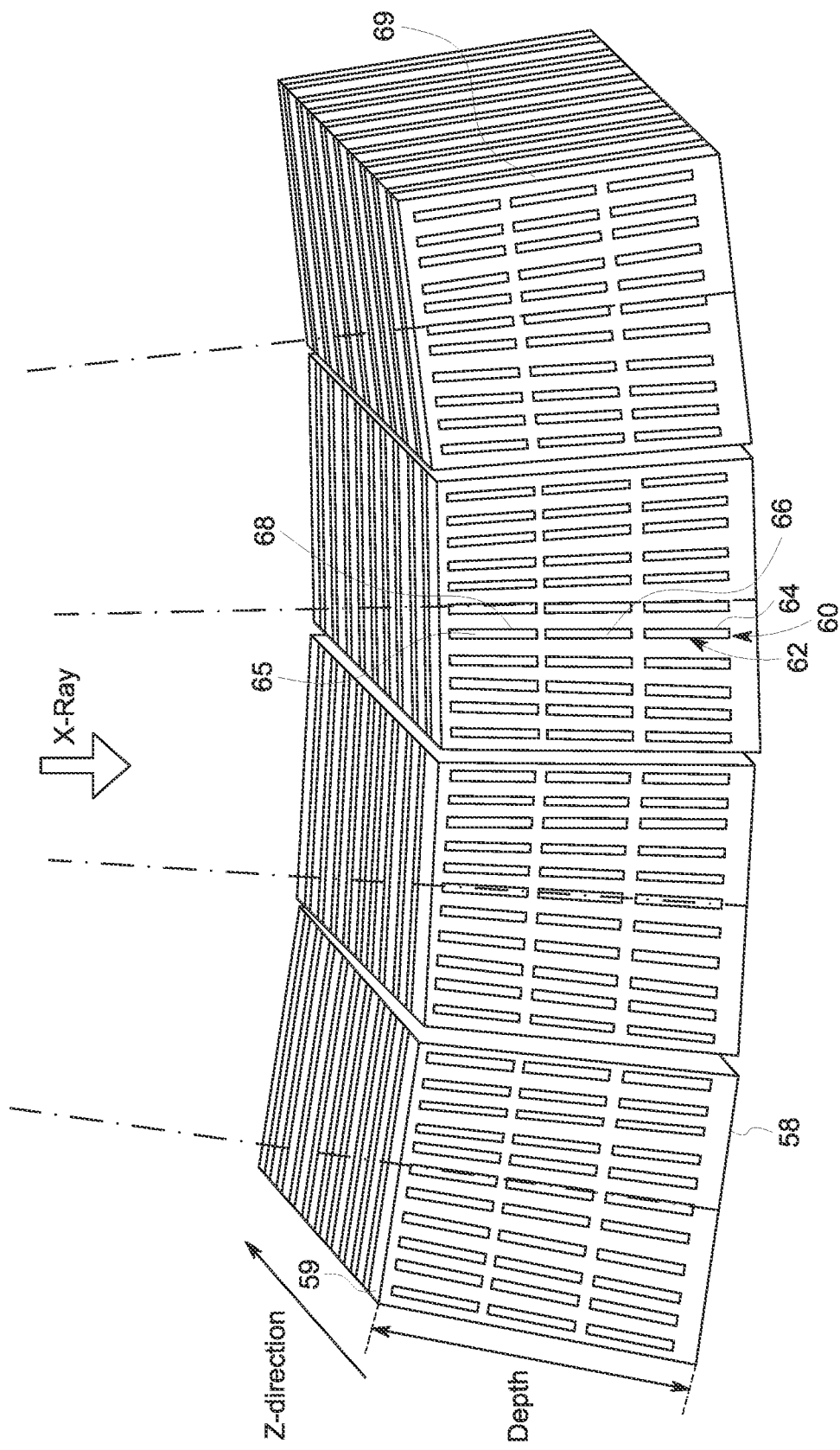
FIG. 2 is a schematic diagram illustrating an example of modular X-ray detector sub-modules arranged side-by-side and stacked one after the other, in accordance with aspects of the present disclosure.

FIG. 2 is a schematic diagram illustrating an example of a modular X-ray detector sub-module 58 (e.g., detector sensors) arranged side-by-side and stacked one after the other. The detector sub-modules 58 may be edge-on detector sub-modules. As depicted, X-rays enter through an edge 59 of the detector sub-module 58. A guard ring may extend along the edges 59 of the detector sub-module 58 to protect the detector sub-module 58 from electrical breakdown and isolate the detector area from excessive leakage current. In certain embodiments, the detector sub-modules 58 may be planar modules. The X-ray detector sub-modules 58 may be stacked one after the other to form larger detector modules that may be assembled together side-by side to build up an overall X-ray detector. The detector sub-modules 58 may generally be arranged side-by-side, e.g., in a slightly curved overall configuration, in a direction substantially perpendicular to the z-direction. In certain embodiments, the detector sub-modules 58 may be stacked one after the other in the z-direction.

As depicted, each detector sub-module 58 includes a plurality of detector elements 60 (e.g., pixels). The detector elements 60 may be elongated electrodes (e.g., metal electrodes) with the length extension directed towards a focal point of an X-ray system. Depending on the detector topology, the detector element 60 may correspond to a pixel. In certain embodiments, the detector sub-module 58 may be a depth-segmented detector sub-module having a number of detector strips 62 with each strip 62 having a number of depth segments 65. As depicted, each strip 62 has a first segment 64, a second segment 66, and a third segment 68 associated with a different depth (relative to the focal point) along a detection line. As depicted, at least portions of each segment 64, 66, 68 are co-linearly arranged. The number of segments 65 may vary (e.g., 1 to 3 or more). For such a depth-segmented detector sub-module 58, each depth segment 65 may be regarded as an individual detector element (if each depth segment is associated with its own individual charge collecting electrode). In certain embodiments, circuitry may treat the depth segments 65 of a single strip 62 logically as a single detector element.

The shape of the detector sub-module 58 may vary. In certain embodiments, the detector sub-module 58 may have a parallelogram shape, a trapezoidal shape, a triangular shape, or another shape. In certain embodiments, one or more edges 59 of the detector sub-module 58 may be slanted. The shapes of the detector elements 60 may vary. In certain embodiments, the detector elements 60 arranged along a slanted side edge 69 of the detector sub-module 58 may include tapered edge segments (e.g., trapezoidal or triangular segments and/or truncated trapezoidal or triangular segments with rounded corners). In certain embodiments, a segment 65 of a strip 62 that is closest to a slanted side edge of a detector sub-module 58 may be orientated so that it extends into an area of an adjacent strip 62. In certain embodiments, the segments 65 may also be slanted.

Figure 3:
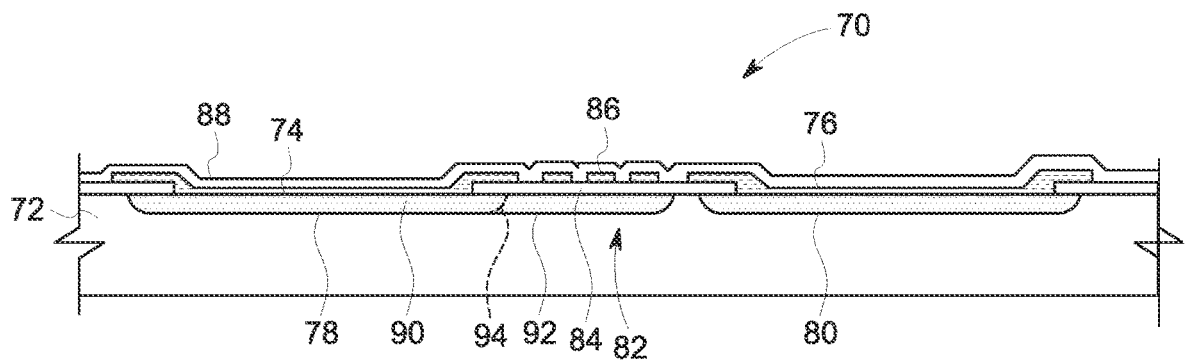
FIG. 3 is a cross-sectional view through a portion of an X-ray detector sub-module, in accordance with aspects of the present disclosure.

FIG. 3 is a cross-sectional view through a portion of the X-ray detector sub-module 70. The X-ray detector sub-module 70 includes a semiconductor layer 72. The semiconductor layer 72 is made of silicon. In certain embodiments, the semiconductor layer 72 may be made of gallium arsenide, cadmium zinc telluride, or another semiconductor material. Detector elements or segments 74, 76 (e.g., metal electrodes) are disposed on the semiconductor layer 72. The electrodes may be made of aluminum. In particular, the electrodes 74, 76 are disposed on doped implants 78, 80 (e.g., p-type or n-type silicon implants depending on whether the silicon of the semiconductor layer is n-type or p-type) that are disposed on the semiconductor layer 72. The detector elements 74, 76 may be respective segments for different strips of segments disposed adjacent to each other. The detector elements 74, 76 and the doped implants 78, 80 are disposed on the semiconductor layer 72 spaced apart so that a gap 82 is formed between them. The X-ray detector sub-module 70 includes an electrical insulator layer 84 extending between—the adjacent electrodes 74, 76. The electrical insulator layer 84 may be silicon dioxide, silicon nitride, polyimide, spin-on glass, or another insulating material. One or more wiring traces 86 (e.g., metal traces) are routed within the gap 84 between the electrodes 74, 76. As depicted, the wiring traces 86 are disposed on the electrical insulator layer 84. As depicted, the wiring traces 86 are disposed in an evenly spaced manner across the gap 84. In certain embodiments, the wiring traces 86 may be routed as close as possible to the edges of the electrodes 74, 76. The wiring traces 86 may be coupled to the electrodes 74, 76 or different electrodes. The wiring traces 86 are routed along the gap 82 (and possibly other gaps) to readout circuitry. As depicted, a passivation layer 88 is disposed over these components of the X-ray detector sub-module 70. The passivation layer 88 may be made of silicon oxide, silicon nitride or another insulator.

Figure 4:
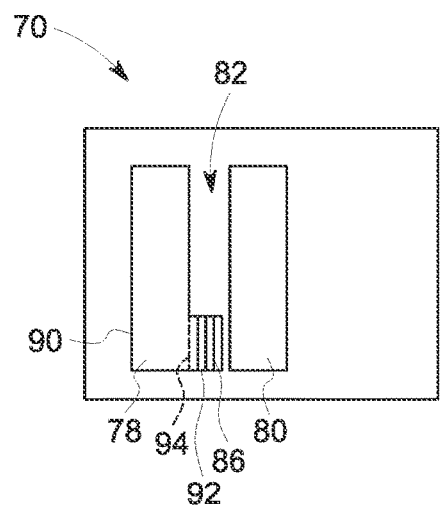
FIG. 4 is a schematic diagram illustrating a portion of an X-ray detector sub-module (with a single p-type implant extension under wiring traces), in accordance with aspects of the present disclosure.

As depicted, the doped implant 78 includes a main or base portion 90 and an extension 92 that extends beyond a normal perimeter 94 (indicated by a dashed line). The extension 92 extends underneath both the wiring traces 86 and the electrical insulation layer 84 in a direction from the doped implant 78 to the doped implant 80. In certain embodiments, the normal perimeter 94 also represents the outer perimeter of the doped implant 78 at a different location of the doped implant 78. The extension 92 of the doped implant 78 acts as a shield for the wiring traces 86 against charges or electrical activity (e.g., due to the absorption of X-rays) in the bulk silicon volume (the semiconductor layer 72). The extension 92 of the doped implant 78 reduces or minimizes the coupling (e.g., electrical coupling) between the semiconductor layer 72 and the wiring traces 86. The extension 92 of the doped implant 78 underneath the wiring traces 86 is depicted in FIG. 4 as well. Only a portion of the wiring traces 86 are shown in FIG. 4. The doped implant 78 may extend underneath the wiring traces 86 along the entire longitudinal length of the implant 78 or only along a portion of the longitudinal length of the doped implant 78.

Figure 5:
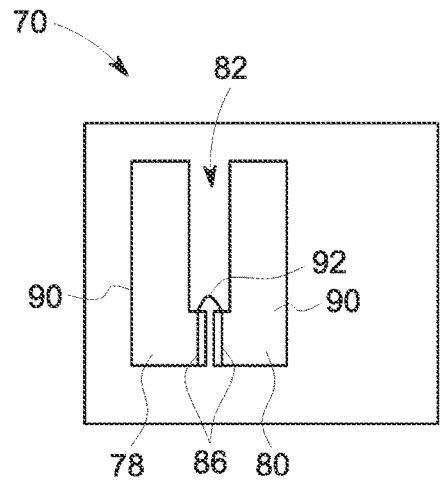
FIG. 5 is a schematic diagram illustrating a portion of an X-ray detector sub-module (with multiple p-type implant extensions under wiring traces), in accordance with aspects of the present disclosure.

In certain embodiments, as depicted in FIG. 5, both doped implants 78, 80 may include extensions 92 that extend within the gap 82 underneath the wiring traces 86. As depicted in FIG. 5, the wiring traces 86 are disposed as close as possible to the edges of the main portion 90 of the doped implants 78, 80 and, thus, the electrodes (as opposed to being evenly spaced across the gap 82). Only a portion of the wiring traces 86 are shown in FIG. 5.

Figure 6:
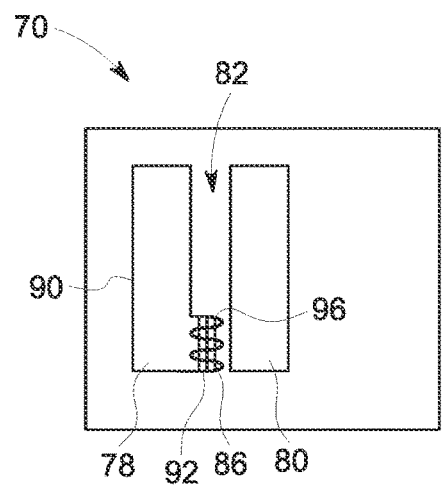
FIG. 6 is a schematic diagram illustrating a portion of an X detector sub-module (with an undulating p-type implant extension under wiring traces); in accordance with aspects of the present disclosure.

In certain embodiments, as depicted in FIG. 6, the extension 92 of the doped implant 78 extending underneath the wiring traces 86 has an undulating shape. In particular, the extension includes multiple spaced apart protrusions 96 extending across the gap 82 from the doped implant 78 towards the doped implant 80. The undulating shape of the extension 92 minimizes the capacitance added to the wiring traces 86 due to the extension 92 being underneath the wiring traces 86. Only a portion of the wiring traces 86 are shown in FIG. 5.

Figure 7:
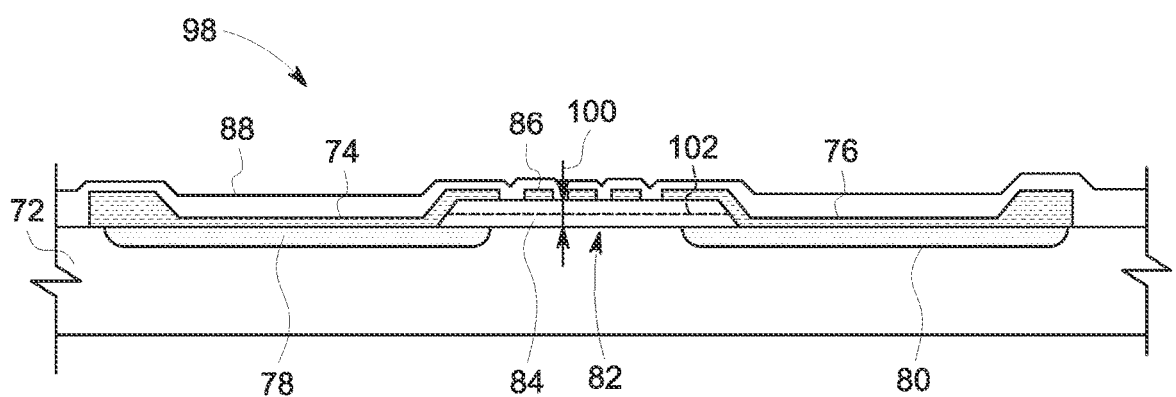
FIG. 7 is a cross-sectional view through a portion of an X-ray detector sub-module (e.g., having a thicker electrical insulation layer between electrodes), in accordance with aspects of the present disclosure.

Alternative techniques may be utilized to reduce coupling (e.g., electrical coupling) between the wiring traces and the underlying semiconductor layer (e.g., bulk silicon). FIG. 7 is a cross-sectional view through a portion of the X-ray detector sub-module 98. The X-ray detector sub-module 98 is similar to the X-ray detector sub-module 70 in FIG. 3 except the doped implant 78 does not extend underneath the wiring traces 86. Instead, the electrical insulation layer 84 is thicker. The electrical insulation layer 84 (e.g., as shown in FIG. 3) is typically approximately 200 nanometers (nm) thick. A thickness 100 of the electrical insulation layer 84 in FIG. 7 may be approximately 2 to 3 times thicker than the electrical insulation layer 84 in FIG. 3. Thus, the thickness 100 of the electrical insulation layer 84 in FIG. 7 may range between approximately 400 to 600 nm. The electrical insulation 84 in FIG. 7 may include a single layer or multiple layers as indicated by dashed line 102. The increased thickness of the electrical insulation layer 84 reduces or minimizes the coupling (e.g., electrical coupling) between the semiconductor layer 72 and the wiring traces 86.

A further technique to reduce coupling between the wiring traces and the underling semiconductor layer may include altering the material utilized for the electrical insulation layer located within the gaps between the pixels. In particular, a material for the electrical insulation layer may be chosen that minimizes electrical coupling even more than silicon dioxide. For example, polyimide may be utilized as the material for the electrical insulation layer.

Figure 8:
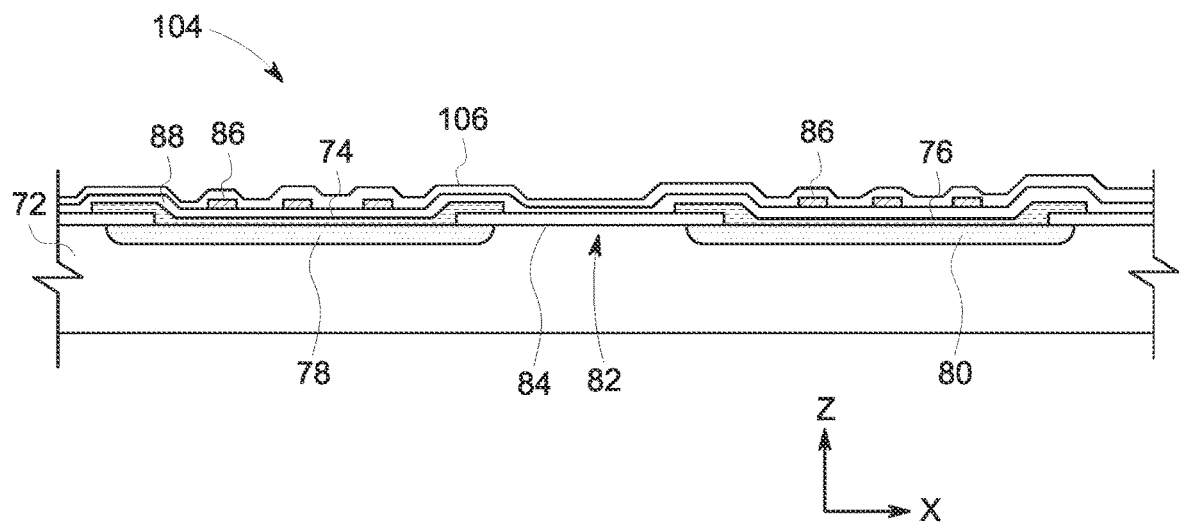
FIG. 8 is a cross-sectional view through a portion of an X-ray detector sub-module (e.g., having wiring traces routed over electrodes in an x-direction), in accordance with aspects of the present disclosure.

As noted above, the arrangement of detector elements on detector sub-modules or sensors (in particular those detector elements along an edge of the detector sub-module or sensor) may result in wiring traces being routed along paths not adjacent to the detector element (e.g., pixel). X-rays absorbed in the detector sub-module or sensor beneath the routing may induce signals on the traces resulting in non-local crosstalk effects (i.e., signals attributed to the wrong detector element). In certain embodiments, to facilitate rerouting of the wiring traces additional layers may be utilized. FIG. 8 is a cross-sectional view through a portion of the X-ray detector sub-module 104. In this embodiment, the electrodes 74, 76 are adjacent to each other (in the x-direction) but part of different strips (e.g., segmented strips) that run from toward a top portion to a bottom portion of the X-ray detector sub-module 104 (in other words, the electrodes 74, 76 are horizontally adjacent or aligned). The X-ray detector sub-module 104 is similar to the X-ray detector sub-module 70 in FIG. 3 except the doped implant 78 does not extend into the gap 84. Instead, the wiring traces 86 are routed over the electrodes 74, 76. An electrical insulation layer 88 (e.g., made of silicon nitride or another material) is disposed over the detector electrodes 74, 76 and the wiring traces 86 are disposed over the insulation layer 88. Rerouting of the wire traces 86 minimizes these non-local cross-talk effects.

Figure 9:
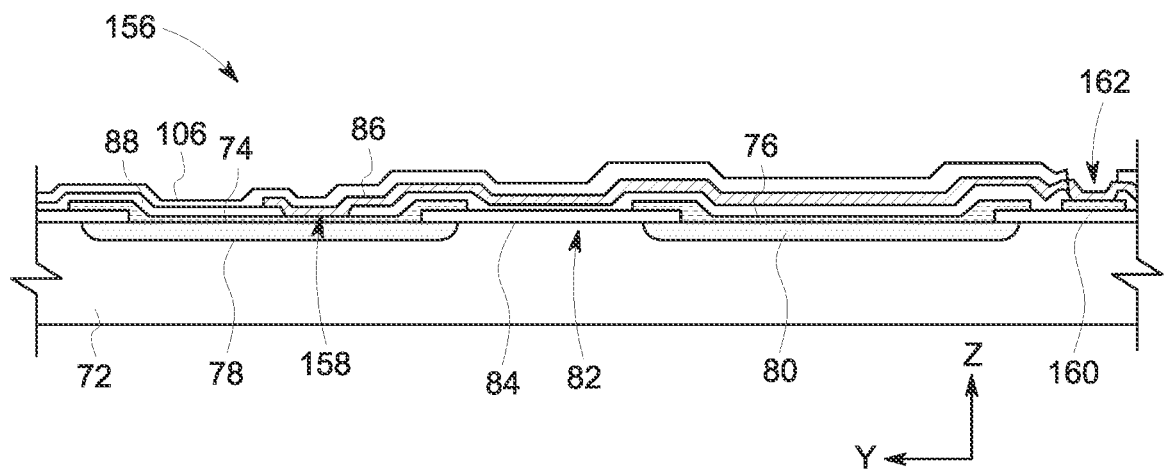
FIG. 9 is a cross-sectional view through a portion of an X-ray detector sub-module (e.g., having wiring traces routed over electrodes in a y-direction), in accordance with aspects of the present disclosure.
Figure 10:
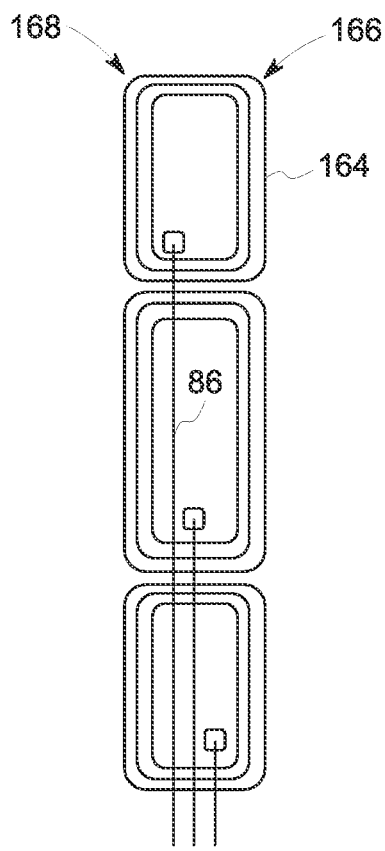
FIG. 10 is a schematic diagram of a portion of an X-ray detector sub-module (e.g., having wiring traces routed over electrodes in the y-direction), in accordance with aspects of the present disclosure.

FIG. 9 is a cross-sectional view through a portion of the X-ray detector sub-module 156. In this embodiment, the electrodes 74, 76 are adjacent to each other (in the y-direction) as part of the same strip (e.g., segmented strip) running from a top portion to a bottom portion of the X-ray detector sub-module 156 (in other words, the electrodes 74, 76 are vertically adjacent or aligned). The X-ray detector sub-module 156 is similar to the X-ray detector sub-module 104 in FIG. 8. The wiring trace 86 is coupled (e.g., electrically coupled) to the electrode 78 thru via 158 through the insulation layer 88. The wiring trace 86 extends over the adjacent electrode 80 (in the y-direction) between the insulation layers 88, 106. Along its path over the various electrodes, the wiring trace 86 may be coupled to a bond pad 160 (e.g., metal bond pad) thru vias 162 through both of the insulation layers 88, 106. FIG. 10 provides a view of wiring traces 86 routed over vertically adjacent detector elements or segments 164 (e.g., electrodes) of a strip 166 for a portion of the detector sub-module 168.

Figure 11:
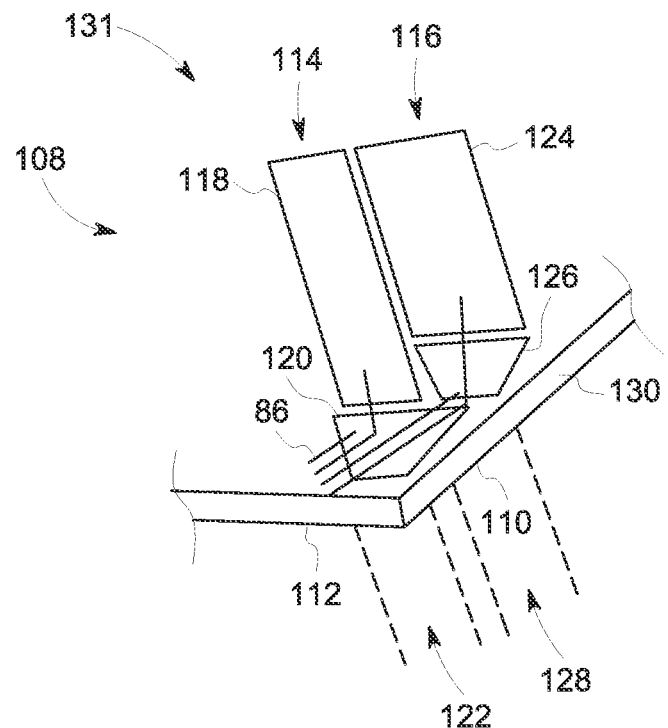
FIG. 11 is a schematic diagram of a portion of an X-ray detector submodule (e.g., having wiring traces routed over electrodes), in accordance with aspects of the present disclosure.

FIG. 11 is a schematic diagram of a portion of an X-ray detector submodule 108 (e.g., having wiring traces 86 routed over electrodes). As depicted, the detector sub-module 108 has a slanted edge or side 110 that forms an obtuse angle relative to another edge or side 112 of the detector sub-module 108. In certain embodiments, the detector sub-module has a slanted edge or side 110 that forms an acute angle relative to another edge or side 112. The detector sub-module 108 includes a first strip of segments or electrodes (e.g., detector elements) 114 and a second strip of segments or electrodes 116. The first strip of segments 114 includes electrodes 118, 120 forming a first detection line (indicated by dashed lines 122) and the second strip of segments includes electrodes 124, 126 forming a second detection line (indicated by dashed lines 128). The electrodes 118, 120 are slanted. The electrodes 120, 126 are located adjacent to a guard ring 130 along the edge 110 of the detector sub-module 108. To avoid having to route the wiring traces 86 between the gaps of the detector elements, the wiring traces 86 are routed more directly over the electrodes 118, 120, 124, 126 (as depicted in FIGS. 8-10) toward and along the edges 110, 112 of the detector sub-module 108 (away from a top portion 131 of the detector sub-module 108). Routing the wiring traces 86 over the detector elements adjacent the slanted edge 110 maintains their detection efficiency since the shape or size of the detector elements are not altered.

Figure 12:
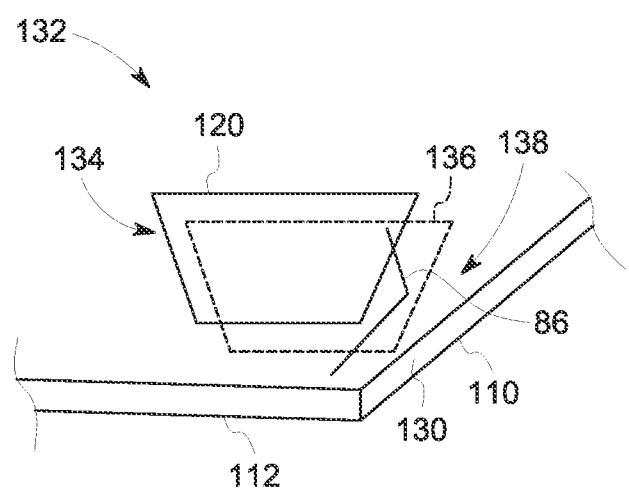
FIG. 12 is a schematic diagram of a portion of an X-ray detector submodule (e.g., having a position change for edge electrodes), in accordance with aspects of the present disclosure.
Figure 13:
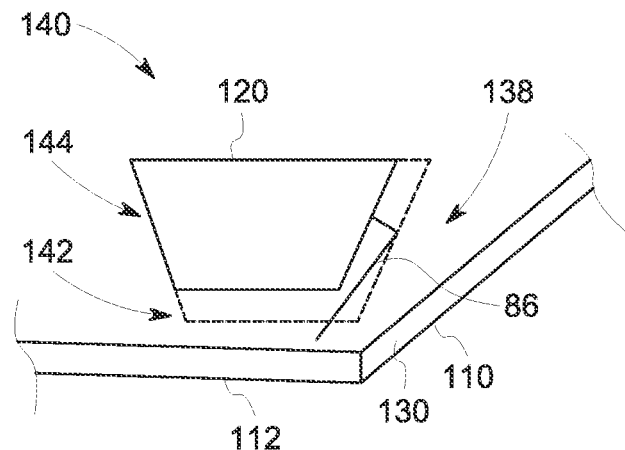
FIG. 13 is a schematic diagram of a portion of an X-ray detector submodule (e.g., having a size change for edge electrodes), in accordance with aspects of the present disclosure.
Figure 14:
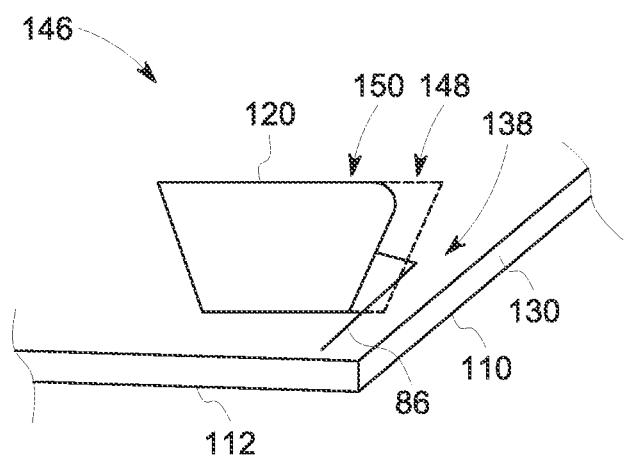
FIG. 14 is a schematic diagram of a portion of an X-ray detector submodule (e.g., having a shape change for edge electrodes), in accordance with aspects of the present disclosure.

In certain embodiments, the wiring traces may be routed along the edges of the detector sub-module within a gap between the detector elements disposed along the edge and the guard ring. As depicted in FIG. 12, for the detector sub-module 132, one or more electrodes 120 disposed along the slanted edge 110 may have a position 134 further away from the edge 110 (compared to position 136 indicated by the dashed outline) to form a gap 138 between the electrodes 120 and the guard ring 130 for the wiring traces 86 to be routed along. In certain embodiments, as depicted in FIG. 13, for the detector sub-module 140, the size of the electrode 120 may be altered from a first size 142 (indicated by the dashed outline) to a second size 144 to create the gap 138 for the wiring traces 86 to be routed along. In other embodiments, as depicted in FIG. 14, for the detector sub-module 146, the shape of the electrode 120 may be altered from a first shape 148 (indicated by the dashed outline) to a second shape 150 to create the gap 138 for the wiring traces 86 to be routed along.

Figure 15:
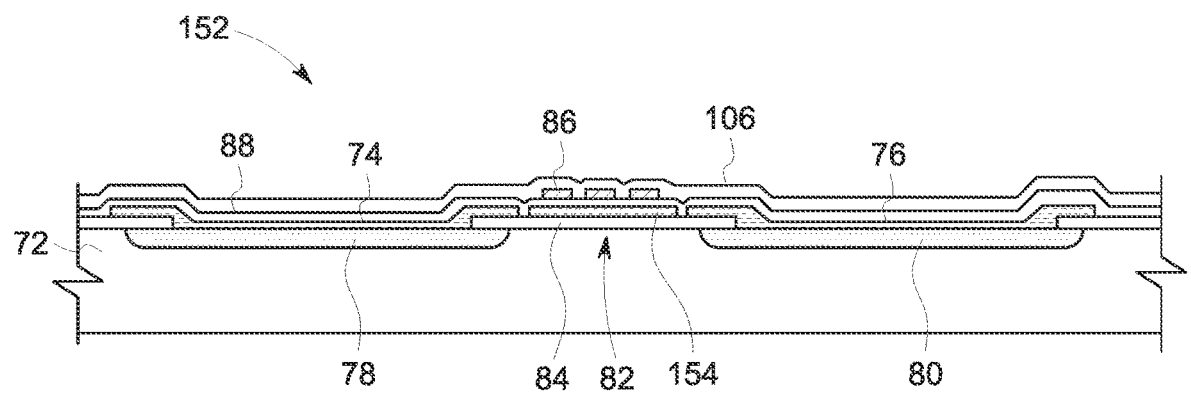
FIG. 15 is a cross-sectional view through a portion of an X-ray detector sub-module (e.g., having a metal shield for wiring traces), in accordance with aspects of the present disclosure.

FIG. 15 provide an alternative way to shield the wiring traces. FIG. 15 is a cross-sectional view through a portion of the X-ray detector sub-module 152. The X-ray detector sub-module 152 is similar to the X-ray detector sub-module 70 in FIG. 3 except the doped implant 78 does not extend into the gap 84. Instead, a metal shielding layer 154 (e.g., made of aluminum or another metal) may be disposed between insulating layer 84 and insulating layer 88 in the gap 82 between detector elements 78 and 80. The wiring traces 86 may then be routed over the metal shielding layer 154 (with the insulation layer 88 underneath) within the gap 82. The insulation layers 88, 106 and the metal shielding layer 154 provide a dedicated layer for the routing of the wiring traces 86.

Figure 16:
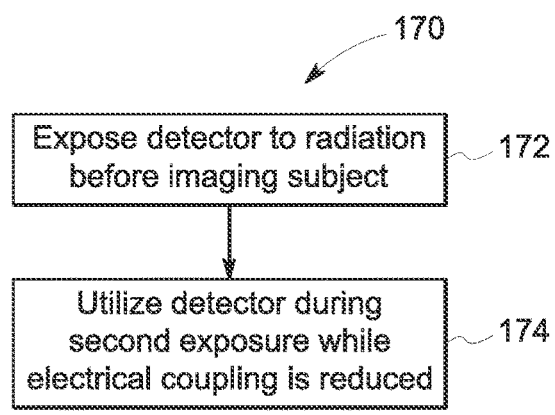
FIG. 16 is a flow diagram of a method for reducing electrical coupling of wiring traces to an underlying semiconductor layer for an X-ray detector, in accordance with aspects of the present disclosure.

As noted above, electrical coupling between the wiring traces and the underlying semiconductor layer (bulk silicon) may be reduced via restructuring of the detector sub-module. Other techniques may be utilized to reduce the electrical coupling between the wiring traces and the semiconductor layer. FIG. 16 is a flow diagram of a method 170 for reducing electrical coupling of wiring traces to an underlying semiconductor layer for an X-ray detector (e.g., edge-on detector as described above). The method 170 includes subjecting the X-ray detector to a first exposure of X-rays prior to imaging an object or subject utilizing the X-ray detector (block 172). In other words, the subject or object is not being exposed to X-rays during the first exposure. This first exposure reduces or minimizes the electrical coupling between the wiring traces and the semiconductor layer (e.g., bulk silicon) underneath the wiring traces by producing an accumulation of slowly moving charge (e.g. positive charge) near the semiconductor layer (e.g., silicon) surface, under the traces. X-ray-induced charges of the same polarity (e.g. positive charge) are then slightly repelled by the accumulated positive charge, and steered away from the traces, reducing the coupling of the charges to the traces. The method 170 also includes utilizing the X-ray detector during a second exposure of X-rays when imaging the object or subject while electrical coupling between the wiring traces and a portion of the semiconductor layer underlying the wiring traces remains reduced due to the first exposure of X-rays (block 174). The second exposure occurs within a time period when the electrical coupling is still reduced or minimized due to the first exposure.

Figure 17:
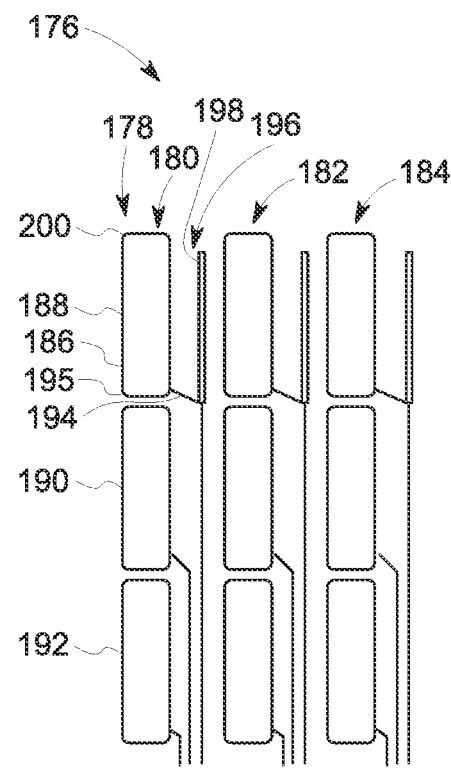
FIG. 17 is a schematic diagram illustrating a portion of an X-ray detector sub-module (e.g., having trace extensions), in accordance with aspects of the disclosure.

To ensure the counting of X-rays, trace extensions may be added to certain spaces on the detector sub-module. FIG. 17 is a schematic diagram illustrating a portion of an X-ray detector sub-module 176 (e.g., having trace extensions). As noted above, each depth segment may be regarded as an individual detector element (if each depth segment is associated with its own individual charge collecting electrode). In certain embodiments, circuitry may treat the depth segments of a single strip logically as a single detector element. As depicted, the detector sub-module 176 (e.g., edge-on detector sub-module) includes a depth-segmented detector sub-module having a number of detector strips 178 (e.g., detector strips 180, 182, 184) with each strip 178 having a number of depth segments 186. As depicted, each strip 178 has a first segment 188, a second segment 190, and a third segment 192 associated with a different depth (relative to the focal point) along a detection line. As depicted, at least portions of each segment 188, 190, 192 are co-linearly arranged. The number of segments 186 may vary (e.g., 1 to 3 or more). Each segment 186 has a respective wiring trace 194 that is routed toward readout circuitry (e.g., and associated with a readout channel). As depicted, the wiring trace 194 extends from a bottom portion 195 of the segment 186. To ensure X-rays that hit within the spaces or gaps 196 between the segments 188 (e.g., top segments) are counted (i.e., to increase sensitivity within these gaps 196), a respective trace extension 198 (e.g., metal trace extension) is coupled to the respective wiring trace 194 coupled to each segment 188. The trace extension 198 extends within the gap 196 in a direction from the bottom portion 195 of the segment 186 toward a top portion 200 of the segment 186.

Figure 18:
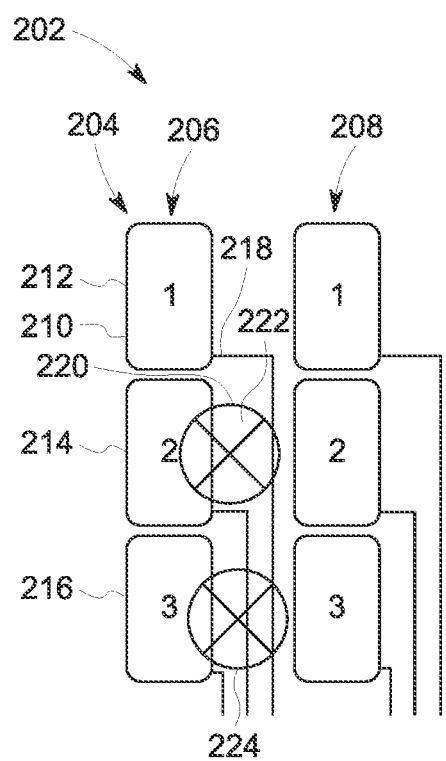
FIG. 18 is a schematic diagram illustrating a portion of an X-ray detector sub-module (e.g., utilizing coincidence detection), in accordance with aspects of the disclosure.

FIG. 18 is a schematic diagram illustrating a portion of an X-ray detector sub-module 202 utilizing coincidence detection to ensure the accurate counting of X-rays and determination of X-ray hit location. As depicted, the detector sub-module 202 (e.g., edge-on detector sub-module) includes a depth-segmented detector sub-module having a number of detector strips 204 (e.g., detector strips 206, 208) with each strip 204 having a number of depth segments 210. As noted above, each depth segment may be regarded as an individual detector element (if each depth segment is associated with its own individual charge collecting electrode). In certain embodiments, circuitry may treat the depth segments of a single strip logically as a single detector element. As depicted, each strip 204 has a first segment 212, a second segment 214, and a third segment 216 associated with a different depth (relative to the focal point) along a detection line. As depicted, at least portions of each segment 212, 214, 216 are co-linearly arranged. The number of segments 210 may vary (e.g., 1 to 3 or more). Each segment 210 has a respective wiring trace 218 that is routed toward readout circuitry (and associated with a readout channel).

Processing circuitry as part of the X-ray detector or the X-ray system utilizes coincidence detection to determine which segment 210 (or segments) within the same strip 204 is triggered by an X-ray hit. As depicted in FIG. 18, a cloud of electrons (depicted by an X within a circle) caused by an X-ray hit 220 represents the X-ray hit 220. Two separate X-ray hits 220 are shown (X-ray hits 222, 224). Assuming trace triggers (by X-ray hits 220) are coincident with charge sharing triggers on the associated pixel (i.e., the X-ray hit 220 hits and triggers both the segment 210 and its respective wiring trace 218 at the same time), coincident detection may be utilized by the processing circuitry to determine where the X-ray hits occurred and what pixels they should be associated with. In addition, the processing circuitry can determine a depth of the X-ray hit 220 along the strip 204 of segments 210. Further, the processing circuitry can associate a single segment 210 with the X-ray hit 220 to avoid double counting (i.e., incorrectly contributing the X-ray hit 220 to a segment 210 due to its respective wiring trace 218 being hit at a location remote form the segment 210). In particular, coincidence detection by the processing circuitry is the logical deduction that the particular combination of coincidently hit channels is consistent with the hit having occurred adjacent to a specific electrode (e.g., segment or detector element).

For example, if the X-ray hit 222 triggered both segment 212 and 214 simultaneously (e.g., due to triggering the wiring trace 218 for the segment 212 at a location remote from the segment 212), the processing circuitry determines that the event (X-ray hit 222) belongs to the segment 214. If the X-ray hit 224 triggered segments 212, 214, 216 (with segments 212 and 214 triggered due to the triggering of the respective wiring traces 218 for the segments 212, 214 at a location remote from both segments 212, 214), the processing circuitry determines that the event (X-ray hit 224) belongs to the segment 216. In other words, the processing circuitry is configured during coincidence detection (when assuming trace triggers (by X-ray hits 220) are coincident with charge sharing triggers on the associated pixel) to assign the X-ray hit 220 to the segment 210 that is adjacent to the most triggered traces of those segments 210 within the strip 204 triggered by the X-ray hit 220. In certain embodiments, the processing circuitry is configured to estimate an energy (i.e., total amplitude of a peak) of the X-ray hit 220 based on a linear combination (e.g., sum) of pulse heights for each readout channel associated with segments 210 and wiring traces 218 triggered by the X-ray hit 220. For example, estimating the energy for the X-ray hit 222 may be a linear combination of the pulse heights for the readout channels associated with both segment 214 and the wiring trace 218 for the segment 210. It should be noted that the X-ray hit 220 may hit multiple segments 210 at the same time.

It should be noted that one or more embodiments for mitigating trace triggering in channels disclosed above may be combined.

Technical effects of the disclosed subject matter include providing systems and methods for mitigating trace triggering of channels (e.g., readout channels) and, thus, mitigating or eliminating crosstalk effects. In certain embodiments, electrical coupling between wiring traces and the underlying semiconductor volume (e.g., bulk silicon) may be reduced. In certain embodiments, the wiring traces may be rerouted. In further embodiments, dedicated layers may be provided for rerouting the wiring traces. In even further embodiments, coincidence detection may be utilized to correctly attribute an X-ray hit to the proper pixel. Overall, these embodiments may reduce false triggering events. These techniques improve the performance of silicon-based photon-counting detectors, such as computed tomography detectors or other suitable types of radiographic X-ray detectors.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112(f). However, for any claims containing elements designated in any other manner, it is intended that such elements are not to be interpreted under 35 U.S.C. 112(f).

This written description uses examples to disclose the present subject matter, including the best mode, and also to enable any person skilled in the art to practice the subject matter, including making and using any devices or systems and performing any incorporated methods. The patentable scope of the subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. An X-ray detector, comprising:
    a plurality of detector sub-modules, wherein each detector sub-module comprises:
        a semiconductor layer;
        a plurality of detector elements, wherein a first detector element of the plurality of detector elements comprises a first electrode disposed on a first doped implant and a second detector element of the plurality of detector elements comprises a second electrode disposed on a second doped implant, the first and second detector elements being disposed on the semiconductor layer adjacent to each other with a gap therebetween; and
        wiring traces extending from one or more detector elements of the plurality of detector elements to readout circuitry, wherein the wiring traces are routed within the gap between the first and second electrodes;
        wherein the first doped implant extends underneath a portion of the wiring traces and is configured to shield the wiring traces from electrical activity occurring underneath due to absorption of an X-ray.

2. The X-ray detector of claim 1, wherein the X-ray detector comprises a photon-counting X-ray detector.

3. The X-ray detector of claim 1, wherein each detector sub-module comprises an edge-on detector sub-module.

4. The X-ray detector of claim 1, wherein a subset of detector elements of the plurality of detector elements are located at a side edge of a respective edge of the detector sub-module.

5. The X-ray detector of claim 1, wherein each detector sub-module comprises an electrical insulator layer disposed on the semiconductor layer and extending between the first electrode and the second electrode, the wiring traces being disposed on the electrical insulation layer.

6. The X-ray detector of claim 5, wherein the first doped implant extends underneath the electrical insulation layer.

7. The X-ray detector of claim 1, wherein the first doped implant comprises a first portion disposed underneath the first electrode and a second portion extending underneath the portion of the wiring traces, wherein the second portion of the first doped implant comprises a series of spaced protrusions extending from the first portion toward the second doped implant.

8. The X-ray detector of claim 1, wherein the second doped implant extends underneath the portion of the wiring traces and is configured to shield the wiring traces from electrical activity occurring underneath due to absorption of the X-ray.

* * * * *